(12) United States Patent
Lea et al.

(10) Patent No.: US 11,422,129 B2
(45) Date of Patent: Aug. 23, 2022

(54) METHOD AND DEVICE TO OPTIMIZE ANALYTE AND ANTIBODY SUBSTRATE BINDING BY LEAST ENERGY ADSORPTION

(75) Inventors: Peter Lea, Toronto (CA); Thomas G. Ewart, Toronto (CA); Stuart X. Carmichael, Toronto (CA); Claude Ricks, Barrie (CA)

(73) Assignee: SQI DIAGNOSTICS SYSTEMS INC., Toronto (CA)

( * ) Notice: Subject to any disclaimer, the term of this patent is extended or adjusted under 35 U.S.C. 154(b) by 1598 days.

(21) Appl. No.: 11/632,872

(22) PCT Filed: Jul. 20, 2005

(86) PCT No.: PCT/CA2005/001142
§ 371 (c)(1),
(2), (4) Date: Feb. 6, 2008

(87) PCT Pub. No.: WO2006/007722
PCT Pub. Date: Jan. 26, 2006

(65) Prior Publication Data
US 2008/0269075 A1    Oct. 30, 2008

(51) Int. Cl.
*G01N 33/543*    (2006.01)

(52) U.S. Cl.
CPC . *G01N 33/54353* (2013.01); *G01N 33/54366* (2013.01)

(58) Field of Classification Search
CPC .................... G01N 33/54353; G01N 33/54366
See application file for complete search history.

(56) References Cited

U.S. PATENT DOCUMENTS

| 3,730,760 A | 5/1973 | Machmiller |
| 4,098,876 A | 7/1978 | Piasio et al. |

(Continued)

FOREIGN PATENT DOCUMENTS

| CA | 2569971 | 12/2006 |
| CA | 2573933 | 9/2010 |

(Continued)

OTHER PUBLICATIONS

Rupcich et al. "Optimization of Sol-Gel Formulations and Surface Treatments for the Development of Pin-Printed Protein Microarrays" Chem. Mater. 2003, 15, 1803-1811.*

(Continued)

*Primary Examiner* — Ellen J Marcsisin
*Assistant Examiner* — Cy R Tamanaha
(74) *Attorney, Agent, or Firm* — TraskBritt

(57) ABSTRACT

The present invention provides a method of making an assay device for conducting an assay to detect a concentration of an analyte in a sample fluid. The assay devices would typically have a substantially planar surface having a series of site specific immobilized calibration spot arrays containing pre-determined quantities of the analyte printed thereon. In addition, a series of site specific immobilized test spot arrays, including capture antibody for binding the analyte protein is printed on the assay device. The method involves first modifying the planar surface to provide hydrophobic binding sites, hydrophilic linking and covalent bonding sites. Then the method requires printing the series of site specific immobilized test spot arrays and the series of site specific immobilized calibration spot arrays on the substantially planar surface. Applying the sample fluid to the assay device is the next step followed by testing a sensitivity of the assay and modulating ratios of the hydrophobic, hydrophilic (Continued)

and covalent binding sites in order to optimize the sensitivity of the assay.

8 Claims, 9 Drawing Sheets

(56) References Cited

U.S. PATENT DOCUMENTS

| | | | |
|---|---|---|---|
| 4,746,668 A | 5/1988 | Sato et al. | |
| 4,778,767 A | 10/1988 | Hummelen et al. | |
| 4,784,157 A | 11/1988 | Halls et al. | |
| 4,804,626 A | 2/1989 | Bellet et al. | |
| 4,810,658 A | 3/1989 | Shanks et al. | |
| 4,978,503 A | 12/1990 | Shanks et al. | |
| 5,082,935 A | 1/1992 | Cruickshank | |
| 5,141,868 A | 8/1992 | Shanks et al. | |
| 5,200,312 A | 4/1993 | Oprandy | |
| 5,585,232 A * | 12/1996 | Farr | 435/6 |
| 5,776,785 A | 7/1998 | Lin et al. | |
| 5,781,289 A | 7/1998 | Sabsabi et al. | |
| 5,824,557 A | 10/1998 | Burke et al. | |
| 5,846,738 A | 12/1998 | Seidel et al. | |
| 5,856,203 A | 1/1999 | Robinson et al. | |
| 6,066,448 A | 5/2000 | Wohlstadter et al. | |
| 6,090,545 A | 7/2000 | Wohlstadter et al. | |
| 6,117,643 A * | 9/2000 | Simpson et al. | 435/7.1 |
| 6,123,687 A | 9/2000 | Simonyi et al. | |
| 6,127,120 A * | 10/2000 | Graham et al. | 435/6 |
| 6,140,045 A | 10/2000 | Wohlstadter et al. | |
| 6,141,096 A | 10/2000 | Stern et al. | |
| 6,154,282 A | 11/2000 | Lilge et al. | |
| 6,187,530 B1 | 2/2001 | Scholin et al. | |
| 6,207,369 B1 | 3/2001 | Wohlstadter et al. | |
| 6,265,176 B1 | 7/2001 | Lin et al. | |
| 6,309,893 B1 | 10/2001 | Deeley et al. | |
| 6,322,990 B1 | 11/2001 | Li et al. | |
| 6,326,489 B1 * | 12/2001 | Church et al. | 536/25.3 |
| 6,379,929 B1 * | 4/2002 | Burns et al. | 435/91.2 |
| 6,476,215 B1 | 5/2002 | Okamoto et al. | |
| 6,403,368 B1 * | 6/2002 | Jan et al. | 435/287.2 |
| 6,410,334 B1 | 6/2002 | Schmolz | |
| 6,449,562 B1 | 9/2002 | Chandler et al. | |
| 6,627,459 B1 | 9/2003 | Tung et al. | |
| 6,673,533 B1 | 1/2004 | Wohlstadter et al. | |
| 6,766,817 B2 | 7/2004 | da Silva | |
| 6,918,404 B2 | 7/2005 | Dias da Silva | |
| 7,026,131 B2 * | 4/2006 | Hurt et al. | 435/7.25 |
| 7,066,586 B2 | 6/2006 | da Silva | |
| 7,098,334 B2 | 8/2006 | Furneaux et al. | |
| 7,118,910 B2 * | 10/2006 | Unger et al. | 435/288.5 |
| 7,285,255 B2 | 10/2007 | Kadlec et al. | |
| 7,396,675 B2 | 7/2008 | Pawlak et al. | |
| 7,846,713 B2 | 12/2010 | Lamont et al. | |
| 2001/0007862 A1 | 7/2001 | Kim | |
| 2001/0021534 A1 | 9/2001 | Wohlstadter et al. | |
| 2002/0015663 A1 | 2/2002 | Goldstein et al. | |
| 2002/0015800 A1 * | 2/2002 | Miyamoto et al. | 427/553 |
| 2002/0061531 A1 | 5/2002 | Le | |
| 2002/0081014 A1 | 6/2002 | Ravkin | |
| 2002/0177182 A1 * | 11/2002 | Selitrennikoff | C12Q 1/18 435/25 |
| 2003/0040125 A1 | 2/2003 | Bernatchez et al. | |
| 2003/0059819 A1 * | 3/2003 | Tzeng et al. | 435/6 |
| 2003/0091477 A1 * | 5/2003 | Paul et al. | 422/104 |
| 2003/0096434 A1 | 5/2003 | Krutzik | |
| 2003/0148542 A1 | 8/2003 | Pawlak et al. | |
| 2003/0157699 A1 | 8/2003 | Jerome et al. | |
| 2003/0162284 A1 * | 8/2003 | Dordick | B01J 19/0046 506/7 |
| 2004/0012780 A1 | 1/2004 | Sharma | |
| 2004/0086423 A1 | 5/2004 | Wohlstadter et al. | |
| 2004/0096914 A1 | 5/2004 | Fang | |
| 2004/0121450 A1 | 6/2004 | Pugia et al. | |
| 2004/0191891 A1 | 9/2004 | Tsinberg et al. | |
| 2005/0048570 A1 | 3/2005 | Weber et al. | |
| 2005/0130120 A1 | 6/2005 | Lambotte et al. | |
| 2005/0163659 A1 | 7/2005 | Duveneck et al. | |
| 2005/0164188 A1 | 7/2005 | Kane | |
| 2005/0181379 A1 * | 8/2005 | Su et al. | 435/6 |
| 2006/0073521 A1 | 4/2006 | Saito et al. | |
| 2008/0131600 A1 | 6/2008 | Lea et al. | |
| 2008/0269075 A1 | 10/2008 | Lea et al. | |
| 2009/0074878 A1 | 3/2009 | Lea et al. | |

FOREIGN PATENT DOCUMENTS

| | | | |
|---|---|---|---|
| EP | 0895082 A | 2/1999 | |
| EP | 1436621 B1 | 2/2010 | |
| JP | 03-503212 A | 7/1991 | |
| JP | 3231970 | 10/1991 | |
| JP | 2942213 | 3/1998 | |
| JP | 11-187900 A | 7/1999 | |
| JP | 2001-272405 A | 10/2001 | |
| JP | 2001-343386 A | 12/2001 | |
| JP | 2002-065274 A | 3/2002 | |
| JP | 2002-509252 | 3/2002 | |
| JP | 2003-035711 A | 2/2003 | |
| JP | 2003-507711 A | 2/2003 | |
| JP | 2005-503556 A | 2/2005 | |
| JP | 2005-506530 A | 3/2005 | |
| JP | 2005-516186 A | 6/2005 | |
| JP | 2005-524829 A | 8/2005 | |
| JP | 2006-506642 A | 2/2006 | |
| JP | 2007-506115 A | 5/2007 | |
| WO | WO 86/00135 | 1/1986 | |
| WO | WO 86/00138 | 1/1986 | |
| WO | WO 86/00141 | 1/1986 | |
| WO | WO 96/09549 | 3/1996 | |
| WO | WO 96/28538 | 9/1996 | |
| WO | WO 98/12539 | 3/1998 | |
| WO | WO-9858745 A1 * | 12/1998 | B01J 19/0046 |
| WO | WO 99/36777 | 7/1999 | |
| WO | WO 01/92870 A2 | 12/2001 | |
| WO | WO 03/025573 A1 | 3/2003 | |
| WO | WO 03/034026 A2 | 4/2003 | |
| WO | WO 2005/031355 A1 | 4/2005 | |
| WO | WO 2006/007722 A2 | 1/2006 | |
| WO | WO 2006/007726 A1 | 1/2006 | |
| WO | WO 2009/070875 A1 | 6/2009 | |

OTHER PUBLICATIONS

Huang et al. "ELISA-based Protein Arrays: Multiplexed Sandwich Immunoassays", Current Proteomics, Jul. 1, 2004, vol. 1, 199-210.*
Wang et al. "A genotyping system capable of simultaneously analyzing >1000 single nucleotide polymorphisms in a haploid genome", Genome Res. Feb. 2005;15(2):276-83.*
Adsorption. (1988). In M. Allaby (Ed.), Illustrated Dictionary of Science, Andromeda. Windmill Books (Andromeda International). Credo Reference: https://search.credoreference.com/content/entry/andidsci/adsorption/0?institutionId=743, one page (Year: 1988).*
PCT International Search Report, PCT/CA2005/000827, dated Oct. 3, 2005.
PCT International Preliminary Report on Patentability, PCT/CA2005/000827, dated Dec. 4, 2006.
PCT Preliminary Report on Patentability, PCT/CA2005/001129; dated Jan. 16, 2007.
International Preliminary Report on Patentability, International Application No. PCT/CA2005/001147, dated Feb. 1, 2007.
Supplementary European Search Report from Application EP05772105.2, dated Aug. 6, 2007.
Huang, Ruo-Pan, Simultaneous Detection of Multiple Proteins with an Array-Based Enzyme-Linked Immunosorbent Assay (ELISA) and Enhanced Chemiluminescense (ECL), Clinical Chemistry and Laboratory Medicine, Mar. 2001, pp. 209-214, vol. 39, No. 3.
Joos et al., A microarray enzyme-linked immunosorbent assay for autoimmune diagnostics, Electrophoresis, 2000, pp. 2641-2650, vol. 21.
Stoll et al., Protein Microarray Technology, Frontiers in Bioscience, Jan. 1, 2002, pp. 13-32.

(56) References Cited

OTHER PUBLICATIONS

Templin et al., Protein Microarrays and Multiplexed Sandwich Immunoassays: What Beats the Beads?, Combinatorial Chemistry and High Throughput Screening, May 2004, pp. 223-229, vol. 7, No. 3.
Kusnezow et al., Abstract, Antibody microarrays: An Evaluation of Production Parameters, Proteomics, Mar. 2003, pp. 254-264, vol. 3, No. 3.
European Examination Report, EP Patent Application No. 05 768 273.4, dated Jan. 19, 2009.
Supplementary European Search Report, EP Patent Application No. 05 768273, dated Apr. 17, 2008.
Wrobel et al., Optimization of high-density cDNA-microarray protocols by 'design of experiments', Nucleic Acids Research, Jun. 15, 2003, p. e67, vol. 31, No. 12.
Office Action for U.S. Appl. No. 11/628,349, dated Jul. 28, 2008.
Office Action for U.S. Appl. No. 11/628,349, dated Dec. 31, 2008.
Office Action for U.S. Appl. No. 11/632,983, dated Apr. 3, 2009.
Bernard et al., Micromosaic immunoassays, Analytical Chemistry, 2001, pp. 8-12, vol. 73.
Wiese et al., Simultaneous multianalyte elisa performed on a microarray platform, Clin, Chem., 2001, pp. 1451-1457, vol. 47.
Office Action for U.S. Appl. No. 11/532,746 dated Dec. 4, 2009.
Kusnezow et al., Antibody microarrays: An evaluation of production parameters, Proteomics, 2003, v. 3, pp. 254-262.
Mann, C.J., Production of Protein Microarrays, Online Jan. 16, 2004 (Jan. 16, 2004), WileyVCH, XP002477008 Retrieved from the Internet:URL:http://www3.interscience.wiley.com/cgi-bin/booktext/107061770/BOOKPDFSTART>[retrieved on Apr. 17, 2008] * p. 172-p. 176  p. 177  p. 183 ** p. 185 * or Mann, C.J., Protein Microarray Technology, Ed. Dev Kambhampati, Jan. 2004, Ch 8, pp. 165-194.
PCT International Search Report, PCT/CA2005/001147 dated Nov. 15, 2005.
Choi, J.W. et al., An integrated microfluidic biochemical detection system for protein analysis with magnetic bead-based sampling capabilities, Lab on a Chip 2, 27-30 (2002.
Woodbury et al., Elevated HGF Levels in Sera from Breast Cancer Patients Detected Using a Protein Microarray ELISA, Journal of Proteome Research, 2002, pp. 233-237, vol. 1.
Kusnezow et al., Solid supports for microarray immunoassays, Journal of Molecular Recognition, 2003, pp. 165-176, vol. 16.
PCT International Search Report, PCT/CA2005/001142 dated Nov. 14, 2005.
Office Action for U.S. Appl. No. 11/632,746 dated Nov. 23, 2011.
Final Office Action for U.S. Appl. No. 11/632,746 dated Jun. 6, 2012.
Office Action for U.S. Appl. No. 11/632,746 dated Jun. 7, 2013.
Communication pursuant to Article 94 EPC dated Sep. 30, 2010, Application No. 05772105.2-2401, (4 pages).
Response to Examiner's Objection dated May 5, 2010, Australian Patent Application No. 2005263229, (12 pages).
Submission of Prior Art dated Oct. 19, 2007, Canadian Patent Application No. 2,573,933, (one page).
Notification of Requisition by the Examiner dated Apr. 1, 2009, Canadian Patent Application No. 2,573,933, (3 pages).
Response to Office Action and Amendment dated Aug. 27, 2009, Canadian Patent Application No. 2,573,933, (12 pages).
Letter Reporting the Notification of Allowance of Grant dated Jan. 12, 2012, Chinese Application No. 200580031583.3, (one page).
The Notication of Allowance of Grant dated Dec. 23, 2011, Chinese Application No. 200580031583.3, (4 pages total).
EPO Communication dated Jul. 17, 2013, EP Application No. 05772105.2-1402/1779112, (one page).
EPO Office Action dated Feb. 3, 2010, EPO Application No. 05772105.2-2401, (3 pages).
Letter Reporting First Office Action dated Feb. 1, 2011, Chinese Application No. 200580031583.3, (7 pages).
Letter Reporting Office Action dated Oct. 25, 2010, Japanese Patent Application No. 2007-521761, (59 pages total).
PCT International Search Report, PCT/CA2005/00142, dated Nov. 14, 20005.
Official Notice of Allowance dated Apr. 14, 2011, Japanese Patent Application No. 2007-521761.
First Office Action dated Jan. 12, 2011, Chinese Application No. 200580031583.3, (5 pages total).
Australian Letters regarding prosecution of Patent No. 2005263229, 19 pages.
Japanese Notice of Reasons for Refusal for Japanese Application No. 2007-521760, dated Sep. 29, 2010, 2 pages with English translation.
Japanese Notice of Reasons for Refusal for Japanese Application No. 2007-521760, dated Apr. 12, 2011, 2 pages with English translation.
European Extended Search Report and Search Opinion Received for EP Application No. 05768273, dated May 13, 2008, 7 pages.
European Communication pursuant to Article 94(3) EPC for European Application No. 05768273, dated Aug. 29, 2008, 1 page.
Japanese Search Report for Japanese Application No. 2007-521760, dated Oct. 7, 2010, 16 pages with English Translation.

\* cited by examiner 50 mM NaHCO3 pH 9.0    50 mM NaHCO3 pH 9.0    50 mM Borate, pH 5.0
                        50 mM Guanidine HCl     50 mM Guanidine HCl

A                      B                      C                      D

METHOD AND DEVICE TO OPTIMIZE ANALYTE AND ANTIBODY SUBSTRATE BINDING BY LEAST ENERGY ADSORPTION

FIELD OF THE INVENTION

The invention relates to assay devices and methods for detecting the presence of antibody in a test sample and algorithmically creating internal standard/calibration curves, for detecting the presence of an analyte in the test sample and to measure the quantity of same.

BACKGROUND OF THE INVENTION

Methods of analysis for immunodiagnostic assays incorporate techniques to measure errors resulting from faulty assay technique when assays are completed. For example, the measure of assay sensitivity characterizes sensitivity by classical statistical analysis based on repeated measurement of low concentration samples to confirm that the sample result is not statistically different from zero. As the standard error incurred is inversely proportional to the square root of the number of actual measurements, this method does not measure the inherent assay sensitivity.

Known in the art analytical sensitivity, is the minimal detectable, or change in concentration, wherein the zero standard is measured several times and the limit of sensitivity becomes a concentration equating to 2-3 SD (Standard Deviation) from M (the MEAN). However, the precision, known in the art as the closeness of individual measures of an analyte in multiple aliquots of a single and homogeneous volume of matrix, may be incorrect by an order of magnitude. The concomitant fitting of any derived calibration curve does not create a true values dose response curve. This results in considerable error in the actual sensitivity of an assay.

To measure the accuracy, known in the art as the closeness of mean test results obtained by the method for the true concentration of the analyte, accuracy is used to define how close the average measured value is to the true value. The difference in measurement is known as the bias or degree of accuracy. Bias may vary over the range of the assay. It is known in the art that methods for measuring this true value need to be developed.

The repeatability or precision of an assay, defined as closeness of individual measures of an analyte when the procedure is applied repeatedly to multiple aliquots of a single homogeneous volume of matrix or the estimated error in an analytical assay, is known in the art as the percentage coefficient of variation (% CV). Automated assay analysis machines can be affected by variations in sample concentration, temperature, heat and edge effects, incomplete suspension of particles and solid phase precipitation. Precision effects also result from fraction separation and counting errors. In optical systems error is due to effects of turbidity, presence of fluorophores, deterioration of lamps and detectors and the deterioration, over time, of reagents. These factors generally lead to significant decreases in signal to noise ratio. Mechanical manipulation errors can result from poor pipetting and instrument stand-by periods.

Therefore, the assessment for precision of any analytical method requires the measurement of variability at known and relevant concentrations by using defined or standard control solutions to create baseline calibration standards. Accurate determination of such calibrators is based on measurement of known concentrations in dilution series at predetermined intervals, which are then interpolated. Commercially available, as well as in-house prepared reference solutions or reference standards are available, but are often calibrated with standard, external or pooled matrices, which may vary considerably from actual patient test samples. Part of the solution to overcome these errors is to plot the precision against a wide range of concentrations to obtain a precision profile, or quantitative calibration of the assay.

Cross reactivity, assay specificity, bias causing interference, alterations in antigen, antibody, binding sites, low dose (competitive assay) and high dose (sandwich assay) hook effects, heterophilic antibody interference, endogenous interfering auto-antibodies, complement, rheumatoid factor, interference in solid phase antibody binding, endogenous signal generating substances, enzyme inhibitors, catalysts and co-factors have also been shown to express confounding activity in assays, including cross reactivity, matrix effects and carry over of sample in automated immunoassay instruments and samplers.

For clinical applications, the quality control samples may not reflect actual concentrations in the patient, may not reflect the spectrum of present analytes and interfere with the sample matrix to no longer reflect the content of the patient samples. The quality control samples may measure performance at discrepant intervals of concentration which may not reflect clinical decision points.

The applicants have developed microarray assays that provide rapid detection of the presence of analytes in a sample. These are described in U.S. patent application Ser. No. 10/856,785 filed on May 28, 2004 entitled "Method and Device for Rapid Detection and Quantitation of Macro and Micro Matrices" which is hereby incorporated by reference. The assays permit rapid quantitative and qualitative measurements of analyte concentration in a sample. The analyte is labeled with a first antibody that is conjugated with a detectable marker. A typical assay device defines a chamber between the loading portion and the reading portion such that a liquid portion of the sample moves from the loading portion to the reading portion by capillary action. Site-specific immobilized arrays of test dots are printed on the reading portion. The test spots include a second antibody that is bound to the surface of the assay device and that is adapted to bind and label analyte. The assay device also has site-specific immobilized arrays of calibration dots containing predetermined amounts of bound analyte for reaction with excess amounts of the first antibody labeled with the detectable marker. Once the conjugated analyte is bound to the test dots, the measure of the analyte in the test dots can be determined by comparison of test dot label intensity with the label intensity of the calibration dots and reading concentration of analyte from appropriate calibration curves.

Immuno-assays in general, depend implicitly on the direct detection and measurement of the signal generated by the number of antigen to antibody adsorption sites. Non-competitive assays identify these adsorption sites by using a secondary labeled antibody, whereas competitive assays measure unoccupied adsorption sites. As immuno-assays are a function of antibody concentration, volume and affinity constants, only if these values are held constant will it be possible to obtain comparatively accurate measurements. The actual quantity of analyte in the sample still needs to be measured. The analyte concentration is measured by comparison to the pre-calibrated concentration site-specific immobilized arrays of internal reference standards.

If pre-calibrated, external reference standard concentrations are used to create external calibration curves, they provide a consistent source of error in the conversion of interpolated detection signal into analyte concentration assumed to be present in the test sample. Further error in antibody to analyte measurement may be induced by the use of a solid support or substrate on which either antigen or antibody is adsorbed. Although enhancing binding charge on the substrate further compounds external reference errors, ambient analyte assays are equally distorted.

Although adsorption to solid support surfaces increases by addition of hydrophobic binding forces, enhancing surface modification can cause changes in protein analyte structure, as well as antibody structure, to significantly alter complex formation. Structural change leading to alteration in complex formation has a direct effect on the quanta of signal e.g. photon counting errors, measured by a detector to determine a label to concentration ratio.

There is therefore a need for a method when testing fluids for analyte, produced under certain conditions, to optimize the diagnostic value of site specific immobilized arrays. There is a need for such a device having secure, repeatable, quantifiable, reproducible, modulated and reliable attachment of site-specific immobilized arrays to a solid support without aberration to improve the sensitivity of such immuno-assays to have a dynamic detection range of femtomol to nanomol per ml analyte concentrations. Modulated substrate surface modification enhances reliable dynamic internal calibration as requested by regulatory agencies, such as the FDA (U.S. Food and Drug Administration).

SUMMARY OF THE INVENTION

The invention relates to a method for test site-specific immobilized arrays, having a captive antibody for binding to an analyte and calibration site-specific immobilized arrays, containing known concentrations of analyte to be printed onto a common surface of an assay device. The assay device is preferably surface modified to enable modulated and site specific quantifiable attachment of requisite molecular species and their aggregates to a surface. A proportion of hydrophilic, hydrophobic and covalent linking sites to binding sites on the surface of the assay substrate in a device are modulated in order to optimize the sensitivity of the assay on an assay specific basis. In the case of multiplexing the modulation of the surface energy is done on an assay pair i.e. antigen/antibody basis.

The immuno-diagnostic device has a solid support, the surface of which has been modified to allow modulation and therefore optimization of countervailing hydrophilic and hydrophobic forces. This modification permits the optimal adsorption of analyte protein and antibody. Printing of site-specific immobilized arrays with diagnostic dots from 5 micrometers to 500 micrometers in diameter, with a preferred range of 50 micrometers to 125 micrometers in diameter, is also a function of constant relative humidity. Surprisingly, internal calibration of a test by printing analyte of known concentrations in site-specific immobilized arrays allows determination of the proportional measurement by use of surplus antibody-detectable marker complexes. The method pertains to this combination of parameters to establish the optimal configuration for obtaining more accurate diagnostic test results.

According to one aspect of the present invention there is provided a method of making an assay device for conducting an assay to detect a concentration of an analyte in a sample fluid, said assay device having a surface, the surface having a site specific immobilized calibration dot including a predetermined quantity of the analyte printed thereon and a test dot including a capture antibody for binding said analyte, said method including the following steps:

modifying said surface to provide hydrophobic binding sites, hydrophilic linking sites and covalent linking sites;

printing said test spots and said calibration dots on said surface;

applying the sample test fluid to the assay device;

testing a sensitivity of the assay; and modulating the ratio of said hydrophobic binding sites to said hydrophilic linking to said covalent sites in order to optimize the sensitivity of the assay.

DETAILED DESCRIPTION OF THE INVENTION

Figure 1:
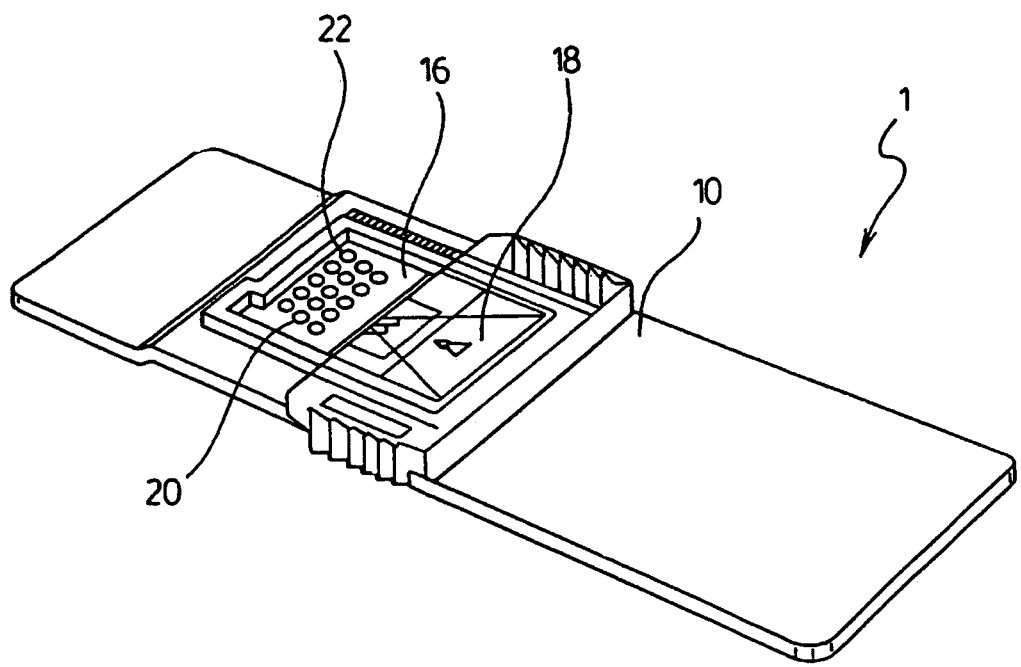
FIG. 1 is a perspective view of an assay device of the present invention for carrying out fixed array tests.

The method of the present invention is preferably carried out in association with an assay device 1 having site-specific immobilized arrays of calibration dots and site-specific immobilized arrays of test dots printed thereon. A preferred assay device 1 is shown in FIG. 1. The assay device 1 has a substantially planar surface 10 that includes a sample loading area 18. The substantially planar surface 10 has printed thereon at least one and preferably at least three of test capture 20 and calibration site-specific immobilized arrays 22 printed in the reading area 16. More preferably a multiplex of site-specific immobilized arrays of test spots for detecting the presence of analytes are printed on the reading area 16. The site-specific immobilized array test spots 20 preferably include bound antibodies that specifically bind to a protein analyte. The bound antibodies are preferably spaced apart as to make each bound antibody available for binding to the test antigen free of stearic hindrance from adjacent antigen complexes. Preferably, a non-reactive protein separates the bound antibodies in each of the site-specific immobilized array test dots.

The reading area 16 has site-specific immobilized arrays of calibration dots 22 printed thereon. The calibration dots contain a pre-determined quantity of said analyte for reacting with unreacted reagent from the vessel that is bound to a detectable marker. The site-specific immobilized arrays of calibration spots allow the intensity of the label to be correlated to the amount of the antigen present. The intensity of label in the site-specific immobilized arrays of test spots is then used to derive the quantity of antigen present in a tested sample volume.

The assay immobilization substrate may be selected from materials which permit surface modification, including silicon, glass and polymeric materials, but in a preferred embodiment is made of plastic support substrate such as polystyrenes and polypropylenes. The polymer surface can be readily modified to adsorb antigen and antibody. Protein adsorption requires hydrophobic binding sites for optimal attachment to the surface of the assay device, whereas antibody binds well to hydrophilic charge linkages, and covalent bonds. These site-specific immobilized arrays of test spots are proportionally adsorbed to the reading area surface as a function of surface modification resulting from increase of unit area effective charge density. Increase or changes in the balance of forces associated with Van der Waal's interactions, hydrophilic and hydrophobic forces and modulation in covalent bond density allows selective enhancement of hydrophilic to hydrophobic properties of the reading area surface and site-specific immobilization of test spot arrays.

The enhanced spread of spot fluid volume, resulting as a modification of contact angle, also is a function of relative humidity and temperature. As the relative humidity increases, drying time of the spots increases which allows larger spot formation on the surface for a similar dispensed volume of test fluid. The net effect results in much thinner spots, thereby approaching the ideal single molecular layer adsorbate which forms a more sensitive molecular layer for optimal analyte capture by the capture antibody. Surprisingly, the even dispersion of analyte throughout the site specific immobilized test spot arrays optimizes test dot morphology in three dimensions.

The analyte to be captured and measured is identified by a label conjugated to an analyte specific marker antibody. Fluorescent dyes are known in the art as detectable markers for providing accurate labeling. Surprisingly, the analyte-antibody-dye complex provides a measure of analyte concentration when equated to a baseline derived from the site-specific immobilized arrays used as standard internal analyte calibrators. In contrast, the use of external calibrators is a major source of accepted error commonly found in immuno-assays.

The excess dye conjugated anti-analyte antibody, which is not bound to the respective analyte, is normally considered to be redundant and is washed away as is known in the art. Surprisingly, this method of the present invention uses the anti-analyte antibody, to create multiple internal, in device calibration lines directly from the site-specific immobilized calibration arrays.

Along with the known capture antibody site-specific immobilized array test dots to capture the analyte, a series of site-specific immobilized array calibration dots is printed directly adjacent to the site-specific immobilized arrays of test dots, as shown in FIG. 1. This second set of site-specific immobilized calibration dots 22 consists of decreasing per dot concentration of known concentration of analyte. Thus the assay, when carried out on the device, has now been reduced to a single step assay, with no mandatory need for intermediary washing steps to remove excess anti-analyte antibody, as the excess of conjugated label antibody background concentration is effectively reduced by binding to the predominant site-specific immobilized array spots containing known concentrations of calibration antigen.

Surprisingly, the process of the present invention provides epoxysilane substrates for immobilized arrays with modulated, covalent, high capacity binding of amino-terminal oligonucleotide libraries, cDNA libraries, proteins, peptides, glycoproteins, lipopolysaccharides, as well as small molecules such as Biotinyl-3,6-dioxaoctanediamine (Pierce, EZ-Link Biotin-PEO-Amine). No organic solvents are used in the process. A fume hood is not required, neither are special disposal precautions. Optimal results are obtained when using printing buffers 3× to 6×SSC pH 7, 0.15M Sodium Phosphate Buffer 8.5, 0.1M Sodium Phosphate Buffer pH 7.2, and 0.1 M Sodium Bicarbonate pH 8.6. Spot size can be adjusted by adding a small amount of detergent (0.01% to 0.05% SDS).

Figure 8:
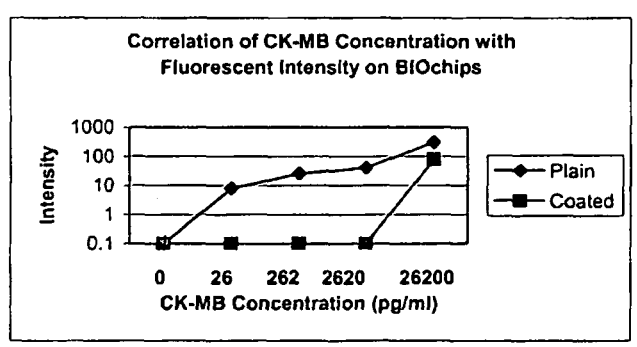
FIG. 8 is a graph showing a correlation of charge density on binding to modified solid support surface.

When the test fluid containing the analyte-antibody-dye complex as well as surplus anti-analyte-antibody-dye complex, is flowed over the two types of site-specific immobilized arrays of test spots printed in the assay device, the surplus complex binds with the known analyte spots to create the reference concentrations for calibration when the dye concentration is read in a reader. The analyte-antibody-dye complex binds with the capture antibody site-specific immobilized arrays of test spots and provides a reading for the concentration of analyte in the test solution. This method of the present invention for Internal Dynamic Calibration (IDC™), integrates a comparative internal calibration standard curve with the comparative test curve as shown in FIG. 8. The actual concentration of test fluid analyte is accurately determined because the test specific internal calibration standard is simultaneously provided.

The method when used in conjunction with the device provides an empirical determination of the correct enhancement of charges induced on the assay device for sufficiently binding assay components without causing loss of detection signal as a result of high density binding events, i.e. number of bonds per unit surface area of the assay device.

In order to attain maximum sensitivity in the assay device of the present invention, the assay device has known concentrations of antigen in the calibration dots. The increasing antigen concentrations are read during the assay as a result of binding with surplus antigen-antibody plus fluorescent label calibration complex. The antigen, whether a requisite protein and or nucleic acid or derivative, needs to be firmly attached to the immobilizing substrate surface of the assay device to prevent becoming soluble and being washed away during the course of the assay process. Attachment of analyte site-specific immobilized arrays of test spots is optimized with a balance of hydrophobic, hydrophilic and covalent linkage, modulated by analyte suspension buffer containing molecular spacer for even dispersion of analyte throughout the printed test spot. Even dispersion ensures even illumination level per test spot and minimizes steric hindrance.

Figure 9:
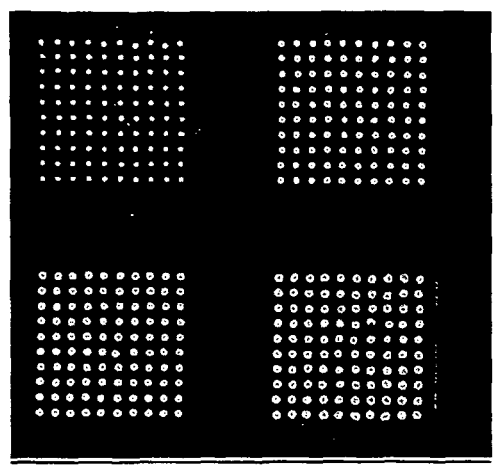
FIG. 9 is a photograph of an assay device showing adequate surface modification of a support surface of the device.

Surprisingly, the degree of surface modification maximal for protein adsorption, may act in reverse for antibody adsorption as shown in FIG. 9. Optimal density of surface charges can attach antibody so firmly to the charge-modified surface to such an extent that although antibody is present, no antigen binding events are found. As a direct consequence, no free antigen-label complex can be captured.

Direct binding of antibodies to a bare surface which has not been substrate modified according to the present invention, may result in conformational antibody changes that reduce their affinity for the analyte. Analytes also passively adsorb onto energized surfaces. The proportion of analyte bound can range from 5% to 95%, so careful optimization of a surface modification and coating process is important. Binding of protein to plastic for example, occurs because water molecules have a much stronger affinity for each other than for hydrophobic regions. The exclusion of hydrophobic sites from the solution causes parts of proteins to adsorb to substrates.

The solid support surface of the assay device is modified to have a balance of hydrophilic enhancement for antibody binding and test fluid flow characteristics versus maintenance of hydrophobic and covalent binding for protein adsorption. Printing, on the modified surface, of the calibration and test dot analytes suspended in modulation buffer containing molecular spacer, is carried out under constant humidity control to ensure that the spots tend to minimal thickness leading to the formation of molecular layer thickness site-specific immobilized arrays of test spots. Key attributes of the modular surface resulting from the present invention, includes maintenance of assay precision, sensitivity and repeatability.

Figure 6:
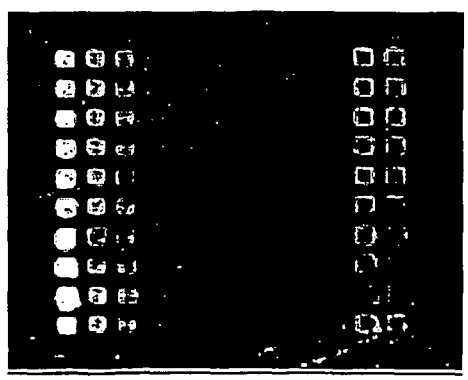
FIG. 6 is a photograph of a top surface of an alternate embodiment of the assay device of the present invention.

As shown in FIG. 6, an internal calibration method of the assay consists of multiple repeats to support high confidence limits for accurate diagnosis. An effective balance of the applied parameters for attachment of the dots to the modified surface is confirmed by performing immuno-diagnosis of test sample fluid. When optimal conditions for a specific assay have been confirmed, mass production commences with quality control tests incorporated at required intervals.

In order to produce consistent, modulating epoxysilane coatings for substrate surfaces, the substrate is cleaned in detergent solution, washed for several hours, then transferred into bleach. The epoxysilane coating is applied as fresh 2-Morpholinoethanesulfonic acid, monohydrate (MES) solution with added 3-Glycidyloxypropyltrimethoxysilane. Excess water is removed from the substrates, and the substrates transferred into Epoxysilane/MES solution. The substrates are washed in preferably 3 but alternatively 1 or 2 changes of DI water and dried. Immediately after epoxysilane coating the substrate surface is hydrophilic. Baking dehydrates the surface without degrading the reactive epoxy groups on the surface yet makes the surface less hydrophilic. The substrates are best stored at room temperature.

This covalent epoxysilane process of the present invention has proven to be the optimal method to produce surface energy modulation as the covalent reaction thermodynamically favours energy minimization and the epoxysilane surface can be modulated using baking time and temperature, to have controlled surface energies (contact angles) from very hydrophilic to moderately hydrophobic.

If the surface tension of the coating is greater than the surface energy of the substrate, the coating will not spread out and form a film. As the surface energy of the substrate is increased, the coating will spread out and form a film but, when dry, will have poor adhesion. Further increases in the surface energy of the substrate will result in easier wet-film formation and better dry-film adhesion.

EXAMPLES

Example 1

Effect of Printing Buffer on Spot Morphology and Binding Capacity

Figure 3:
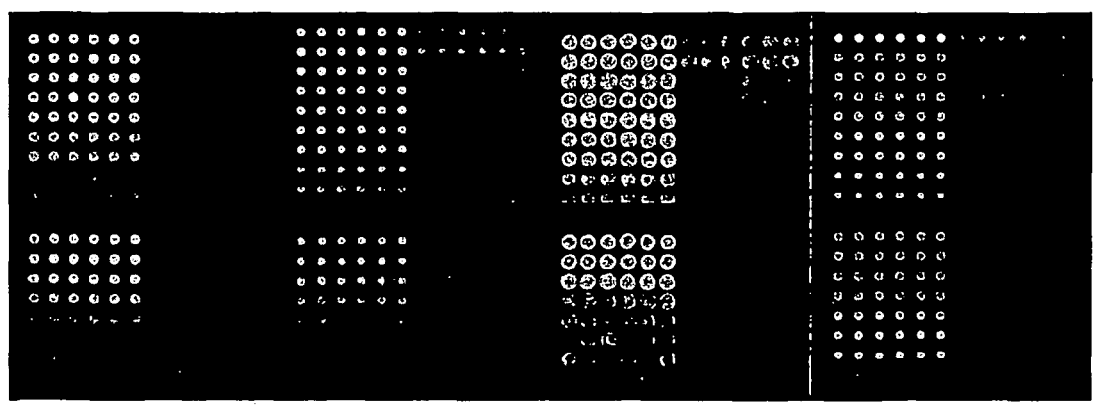
FIG. 3 is a photograph of a top surface of an assay device of the present invention showing a mean fluorescence intensity of spotted BSA.RB conjugate dilutions.
Figure 4A:
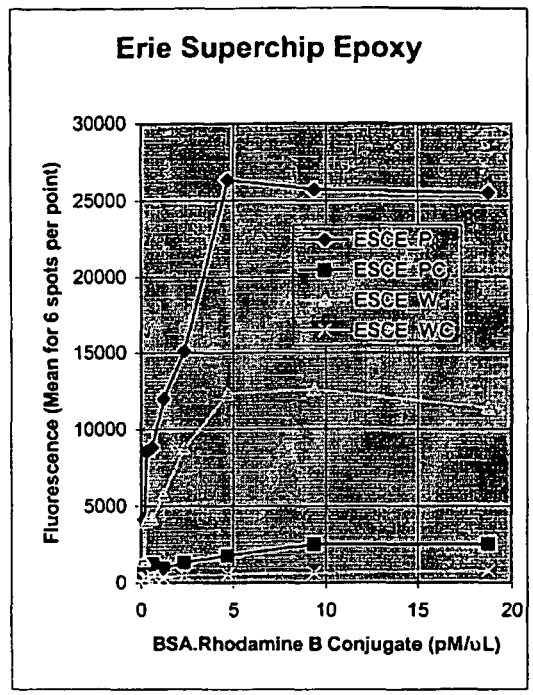
FIG. 4A is a plot of a mean fluorescence intensity of spotted BSA.RB conjugate dilutions with Erie Superchip Epoxy.
Figure 4B:
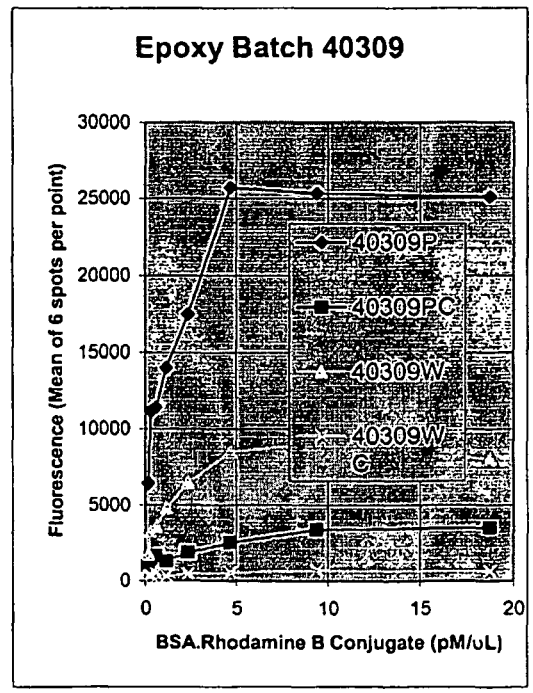
FIG. 4B is a plot of a mean fluorescence intensity of spotted BSA.RB conjugate dilutions with Erie Superchip Epoxy with Epoxy Batch 40309.
Figure 4C:
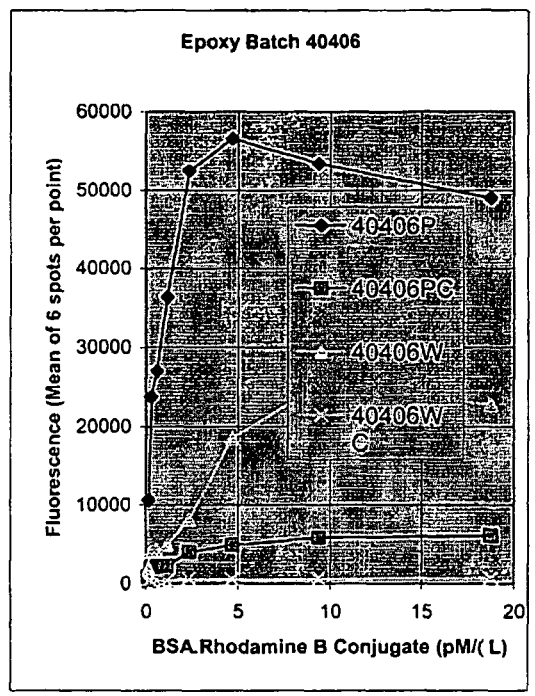
FIG. 4C is a plot of a mean fluorescence intensity of spotted BSA.RB conjugate dilutions with Erie Superchip Epoxy with Epoxy Batch 40406.
Figure 4D:
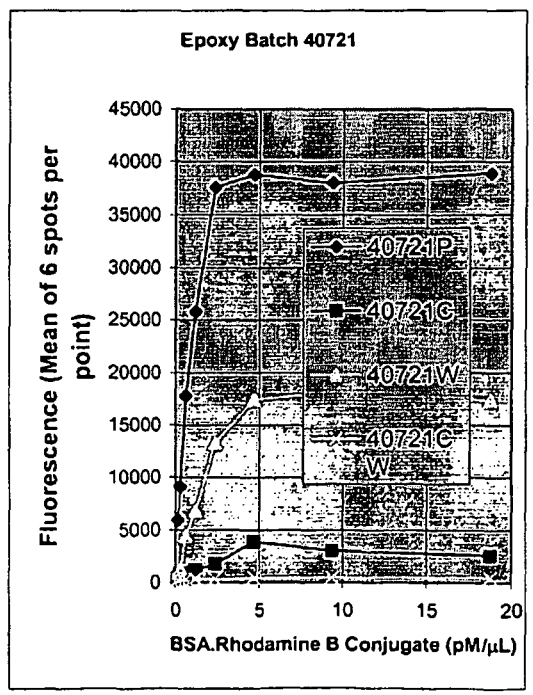
FIG. 4D is a plot of a mean fluorescence intensity of spotted BSA.RB conjugate dilutions with Erie Superchip Epoxy with Epoxy Batch 40309.

With respect to the Epoxy surface, FIG. 3, 0.150 M Phosphate buffer again produced the best results. 10% Glycerol gave the lowest signals. For this surface also 50% DMSO showed false signals in the blank spots. Overall signal intensities and binding capacities are quite evidently less than those for the corresponding Hydrogel-Epoxy surface at all BPA concentrations, and in all buffers.

Figure 2:
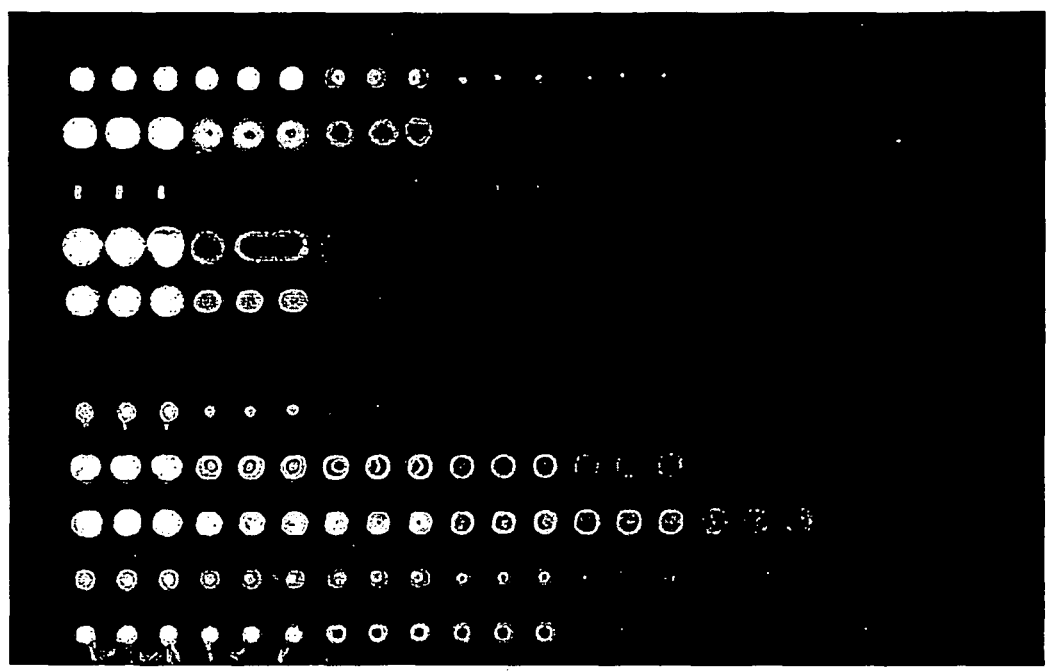
FIG. 2 is a photograph of a top surface of an assay device of the present invention showing a spot morphology of ten different print buffers on epoxy substrate.

FIG. 2 shows a dot morphology of 10 different print buffers on epoxy substrate. Eight dilutions (5×) of BPA were printed in triplicate from the maximum of 1000 µg/ml at left to 0.0 at right. Substrate was blocked with blocking buffer for 2 hours. Bound BPA was reported by treatment with 4 µg/ml Streptavidin-Cy3 in the same blocking buffer for 1 hour. Phosphate pH 8.5 10% DMSO/Water Blank 50% DMSO/Water 10% Glycerol/Water Blank MES pH 4.7 Borate pH 9.3 Carbonate pH 9.66×SSC pH 7.23×SSC pH 7.2 Water Example 2

Printing Optimization and Quality Control for Covalent Binding Microarray Substrates A number of methods are generally accepted for quality control of pin-printed microarrays. In a printed library of oligo or cDNA arrays, spot morphology and missing spots can be visualized with DNA intercalating dyes such as SYBR 555 (Invitrogen/Molecular Probes P32930), and by hybridisation with AlexaFluor dye-labeled random 9-mers (Invitrogen/Molecular probes P32934, and P32937). Trace DNA with a fluorescent label that is not excited by either of the standard green or red laser wavelengths may be added to every oligo or cDNA of the library. This is ideal and provides quantitation of the DNA in each spot concurrently with the hybridisation signals, read in a confocal microscope with a third laser and interference filter for the labeled tracer.

Prior to taking the effort and expense of printing a library on batches of substrates it is preferred to check the batches themselves for binding capacity, spot morphology, and batch-to-batch uniformity.

Whether printing solutions of oligonucleotides, cDNA, proteins or small molecules on microarray substrates there is an optimal concentration for the solution. Each surface has a maximum binding capacity. Printing in excess of this wastes precious material, and may cause higher background levels plus increased carryover or cross-contamination of the library. Printing less than the optimum amount produces lower signals and potentially lower signal to noise ratios.

BSA.Rhodamine B conjugate (BSA.RB). Rhodamine B Isothiocyanate (RBITC, Sigma-Aldrich #283984) is a fluorophor that absorbs the green laser wavelength used for Cy3, and emits over a broader spectrum in both Cy3 and Cy5 channels of standard scanning confocal microscopes. Six mg of RBITC was dissolved in 600 microL Ethyl Lactate. Three 1 ml aliquots of Bovine Serum Albumin (BSA, Sigma-Aldrich #A7517), 20 mg/ml, were prepared in Carbonate/Bicarbonate buffer pH 9.6. Each aliquot was mixed with 100, 200 or 300 microL of the RBITC solution and allowed to react overnight. The reaction was quenched by adding 10 mg of Lysine to each of the aliquots and letting it react for 2 hours. A minicolumn was packed with Sephadex G50 and washed with 3×SSC. Each aliquot was gel filtered on the G50 column, and eluted in 3×SSC, the intended microarray printing buffer. The first colored peak (the BSA.RB conjugate) was collected and the later peaks discarded. The conjugation ratios resulting from the increasing ratios of RBITC were estimated from the comparative absorbance spectra of pure BSA, pure RBITC and the conjugates to be approximately 2:1, 5.5:1 and 12.8:1 dye molecules per BSA molecule.

The 5.5:1 conjugate was selected for printing on the following basis. BSA has about the same molecular weight as a 200-mer strand of cDNA to occupy about the same surface area as a 70-mer oligo probe hybridized to a 200-mer target. In addition, the recommended nucleotide/dye ratio for hybridizing labeled transcripts is about 40:1, or 5 fluorophors per 200-mer. Thus, the BSA.RB conjugate molecule simulates the binding surface area per molecule of a probe oligo and the fluorescence labeling of the target expected in a microarray. The 70-mer oligos of the Qiagen/Operon libraries are amino-terminated for covalent reaction with active surfaces such as Epoxy, Aldehyde and NHS ester. The superficial lysine residue amino groups of BSA that have not reacted with RBITC are available to react with the surface via the same chemistry.

The recommended printing concentration for the Qiagen/Operon 70-mer oligo libraries is 15 microMolar (15 pM/microL). A 2× serial dilution of the BSA.RB conjugate in 3×SSC was prepared in a 384 well plate such that blanks (just the 3×SSC buffer alone) alternated between conjugate dilutions. This was designed to test the washing of the array printer pins and determine the severity of well-to-well carryover or cross-contamination. The starting concentration was therefore adjusted to be slightly higher than recommended, 18 pM/microL.

Epoxysilane covalent coated slides of the present invention and samples of Erie SuperChip Epoxy provided by the manufacturer were printed from the 384 well serial dilution plate with Point Technologies tungsten split pins by a Perkin Elmer SpotArray. The wash solution was 10% Ethanol in RO water, the SpotArray being set up for 3 cycles of 2 seconds of jet wash followed by 2 seconds of vacuum drying between wells. Dots were spaced 340 microns apart 12 spots per row, 6 replicates of each BSA.RB dilution followed by 6 replicates of the corresponding blank on the same line, as shown in FIG. 3.

FIG. 3 shows commercial epoxysilane covalent binding microarray substrate (left) and three in-house made batches printed with serially diluted BSA.Rhodamine B conjugate imaged before (top) and after (bottom) washing for 24 hours with 1% ethanolamine+1% BSA pH 8.5 blocking buffer. The top and bottom images of each set were scanned at the same laser and gain settings but are not the same for all sets.

The BSA.RB dilution arrays were scanned on a Perkin Elmer ScanArray Express confocal laser microscope. Typically settings were laser 60%, photomultiplier 55% but were not exactly the same for all slides. These pre-wash tif files were saved for subsequent analysis. The slides were washed for 24 hours in blocking buffer (1% ethanolamine+1% BSA adjusted to pH 8.5 with HCl), then scanned again at the same settings to obtain the post wash image files. Before and after washing images were analyzed with ScanAlyze (EisenLabs, Stanford). Grids and circles were adjusted optimally for each array such that the circles exactly enclosed the fluorescent spots.

Analysis of Protein Retention and Carryover:

Depending on the batch, spots ranged from 160 microns to 250 microns in diameter as seen in FIG. 3. Washing of the pins was not complete as one can clearly see six fainter spots to the right of the six spots of each dilution of BSA.RB conjugate. This can cause cross-contamination of the libraries, limiting the number of printings that can be performed before the library must be discarded. It underlines the importance of making aliquots of the libraries to extend their useful life and reduce costs.

FIGS. 4 A, B, C and D show the plotted fluorescence intensities of the dots versus the printed (pre-wash) concentration of the BSA.RB conjugate (upper purple curve in each chart) and their corresponding neighboring blanks (lower purple curve in each chart). The figures also show the post wash conjugate retention curve (upper dark) and blank (lower faint). At the concentration recommended by Qiagen/Operon for the printing of their 70-mer libraries (15 pM/µL) the carryover is quite high. Analysis shows that printing at this concentration yields lower retained protein than printing at about 5 pM/µL (⅓ the concentration). Thus library material is wasted. Further, the carryover/cross-contamination is higher at the higher concentrations as more protein or oligonucleotide is carried from well to well on the pins even after thorough washing.

TABLE 2

Summary of numerical analysis from the charts in FIG. 2, from which the optimal printing concentration range can be seen to be between 2.5 and 10 pM/µL. Over this range maximum retained protein (signal) is maintained while carryover is reduced.

| Substrate | % Retention 100*(P/W) between 2.5 - 10 pM/□L | % contamination 100*(WC/W) between 2.5 - 10 pM/□L |
|---|---|---|
| ESCE | 47-58 | 4.7-5.8 |
| 40309 | 33-37 | 6.1-7.4 |
| 40406 | 16-47 | 2.5-7.7 |
| 40721 | 35-48 | 2.5-2.7 |

Figure 5:
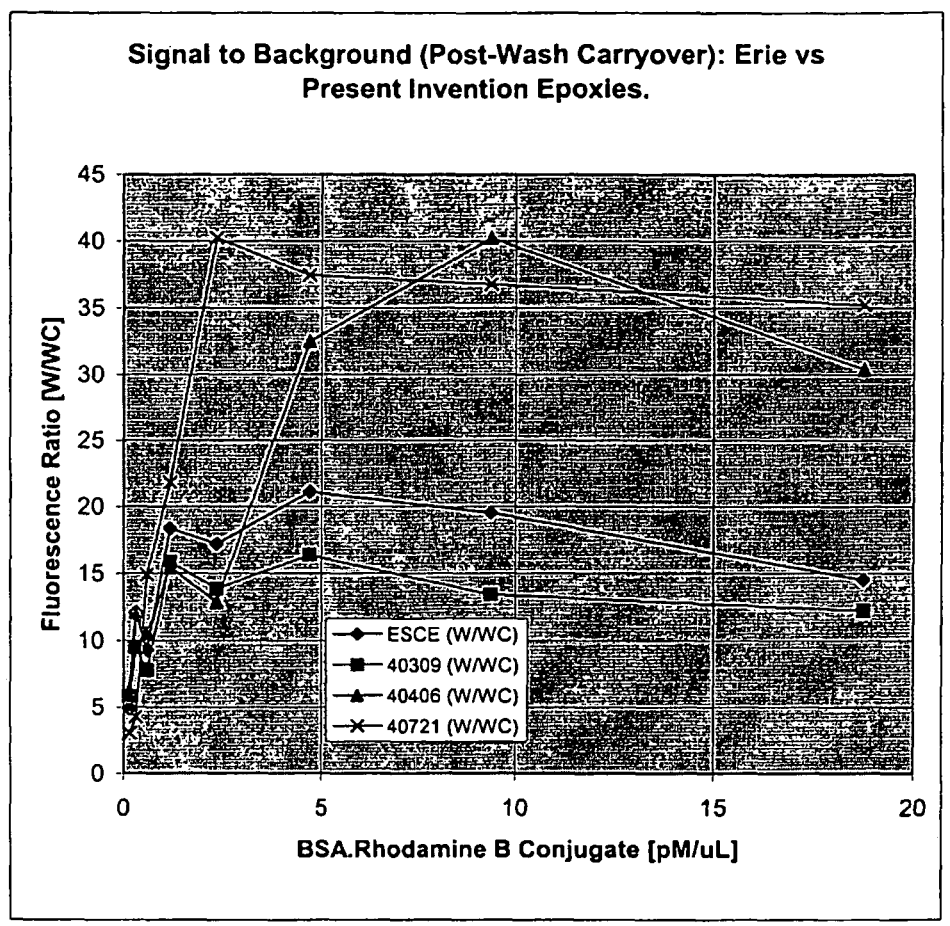
FIG. 5 is a plot of the ratios of mean fluorescence intensities of spotted BSA.RB conjugate dilutions post washing (W) over the mean fluorescence intensities intervening blanks post washing (WC) for ERIE and three batches of Epoxysilane of the present invention.

FIG. 5 shows plots of the ratios of mean fluorescence intensities of spotted BSA.RB conjugate dilutions post washing (W) over the mean fluorescence intensities intervening blanks post washing (WC) for ERIE and 3 batches of Epoxysilane of the present invention, as analyzed by ScanAlyze. Averages are of 6 replicates before and after washing as shown the images of FIG. 1. (Key: P—printed BSA.RB dilution, PC—printed blank carryover, W-BSA.RB dilution post wash, WC—blank carryover post wash.)

Direct printing of fluorophor-labeled proteins or 70-mer oligos is a rapid method of checking the binding capacity or percent retention of least energy adsorption substrate binding for pin-printed microarrays. Different batches of slides may be compared for binding and spot morphology before being accepted for printing of precious libraries. In addition it is a valuable method of assessing both the quality of pin washing, and setting the optimal printing concentration for libraries. Determining optimal printing concentration or maximum signal for minimum concentration and carryover conserve libraries and extends their life by minimizing cross-contamination. Based on these studies our 600 pM Operon/Qiagen human 70-mer library was split into 4 aliquots of 150 pM each. Three were preserved for printing the whole 22K (version 2.1.2) library, and one was used for picking focused subsets of 200 to 800 oligos for protease, breast cancer-related, ring finger protein, clock (circadian rhythm-related), and HOX genes. These subsets were further split into 75 pM duplicates.

Three batches of epoxysilane of the present invention and a commercial Epoxysilane slide (Erie SuperChip Epoxy) are presented as examples of this method. Spot morphologies can be significantly out of tolerance (e.g. batch 40406) even though binding capacity may be acceptable.

Maximum signal and protein retention falls in the printing concentration range 2.5 to 10 pM/microL for all slides in this experiment. This approximate optimal range has also been found in other experiment with oligonucleotides from 9-mers to 70mers (data not shown). Printing at higher concentrations in fact reduces signals and retention presumably by stearic hindrance. Epoxy substrates of the present invention provided the optimum signal to background ratio, an up to 2 times improvement over the commercial substrate in the optimal printing range, and this is evident in the images of FIG. 3.

Example 3

Multiple Site Specific Immobilized Calibration and Test Arrays

Multiple arrays of spots have been adsorbed onto the modified solid support surface substrate.

As shown in FIG. 6, an embodiment of the assay device shows ten printed columns of calibration dots 22 of the same analyte concentration. The final two columns of test dots 20, on the right, are capture antibody dots with adsorbed test samples of concentration to be determined. Each row represents a single assay with internal dynamic calibration (IDB). The test row is repeated ten times. The entire test matrix is 10 dots×10 dots for IDB and 2×10 dots for test samples. The measured fluorescence intensity determines the relative concentrations of analyte.

Example 4

Dynamic Internal Calibration

Figure 7:
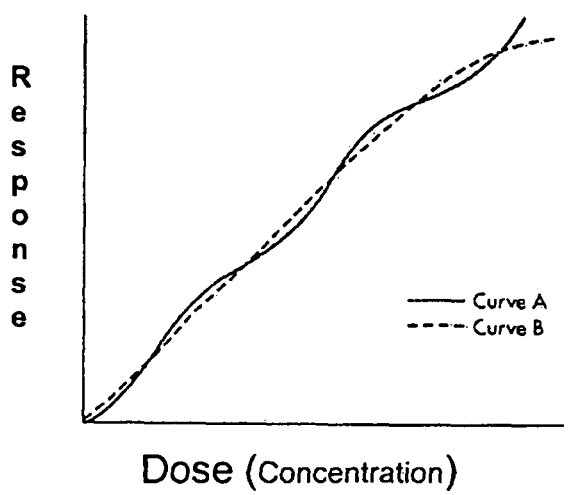
FIG. 7 is a graph depicting dose/response curves to realize an internal dynamic calibration curve.

As shown in FIG. 7, curve A represents the typical variations in dose response when test samples are measured using an internal, generated concentration curve. Curve B is the derived external calibration line, erroneously interpolated as determined by a measured low dose external calibration reading and a high dose external calibration reference reading. The respective values in between the low and high points are then integrated by drawing a line i.e. curve B. The Internal Dynamic Calibration produces a line plot based on several plots resulting in a curve that represents the actual calibrated response of the test sample as in FIG. 8.

Example 5

Device Tested to Compare the Effect of High Density Surface Charge with Optimal Surface Modification with a Balanced Charge To compare dose response of optimized device solid support (upper "Optimal" curve) against highly charged solid support modified surface (lower "Charged" curve). The dynamic spot CK-MB analyte protein concentration ranged from 26 picogram/ml to 26,200 picogram/ml as shown in FIG. 8. The highly charged surface area effectively prevented analyte binding at concentrations less than 2620 picogram/ml.

Example 6

Method Applied to Production Test Device

FIG. 9 illustrates a typical device surface, modified to show comparative print array matrices and to confirm adequate surface modification of solid support for both analyte and antibody adsorption. The method compares relative dot sizes with increment in dispensed dot volume.

Example 7

Humidity Dot Size

Surface modified solid supports were tested for hydrophilic flow effects at 24° C. at 18% humidity and 47% humidity. Dots were measured for comparative increase in diameter. Surface area increased by 51% at higher humidity for the same volume of spot fluid, approximating a 50% reduction in spot thickness.

Example 8

Figure 10:
FIG. 10 is a photograph showing a site specific immobilization of array dots comparing clumped, variegated, annular and evenly spaced distribution of analyte within a dot.
Figure 10:
Figure 10:
Figure 10:
Figure 10:
Figure 10:
Figure 10:

Site Specific Immobilization of Array Dots Containing Evenly Spaced Distribution of Analyte within a Dot FIG. 10 character A, shows the effect of using bicarbonate buffer at pH 9.0 to form a central aggregate of concentrated analyte which causes an emission peak and erroneous data results. Character B shows the effect of additional guanidine hydrochloride which causes dispersed analyte aggregates. Character C shows the use of borate and guanidine hydrochloride at pH 5.0. The formation of an annulus of analyte at the perimeter of the spot, leaving the centre a minimal concentration is shown. Surprisingly, the molecular spacer component of the present invention, FIG. 10 at character D forms the best spot morphology and signal. The analyte is evenly dispersed throughout the spot using borate (50 mM $H_3BO_3$, pH 5.0), but adding Magnesium Chloride (50 mM $MgCl_2$) to actively space the analyte throughout the spot.

The modulated epoxysilane substrate of the present invention, when used in conjunction with analyte and substrate incompatible buffers, immobilizes array spots containing defective, definitive patterns of analyte and analyte aggregates as shown in FIG. 10. Molecular aggregation and dispersion of analyte in array spots is critical when obtaining comparative measurement of analyte concentration. The CV % (percent co-efficient of variance) acceptable in clinical diagnoses is only obtained when the array spots contain an even analyte dispersion, as shown in FIG. 10 at character D. The best dot morphology and signal on nearly every surface was most often obtained with 50 mM $H_3BO_3$, pH 5.0, in most cases with 50 mM $MgCl_2$ added.

Example 9

Immobilization of Nucleic Acid on the Epoxysilane Substrate of the Present Invention The arrays are a focused set of 72 oligonucleotides from the Operon mouse genome library, site specific localized on the epoxysilane substrate of the present invention. The substrate was blocked in 2 mg/ml 2-aminoethanol+1% BSA for 24 hours, then washed with de-ionized water and spun dry.

Figure 11:
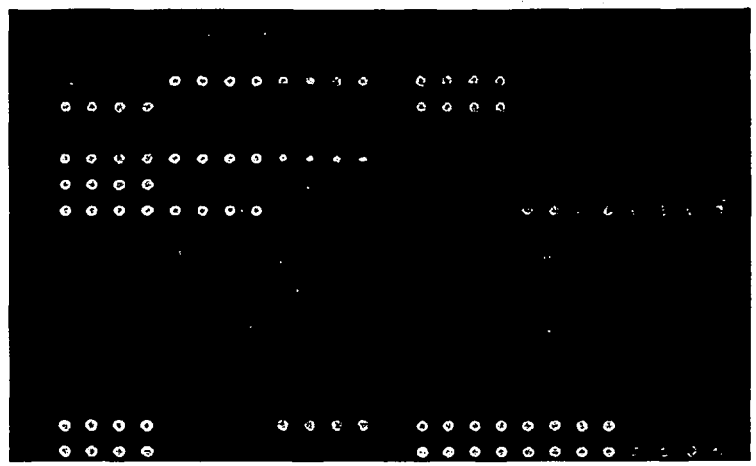
FIG. 11 is a photograph showing mouse embryo site specific immobilized hybridized oligonucleotides.
Figure 12:
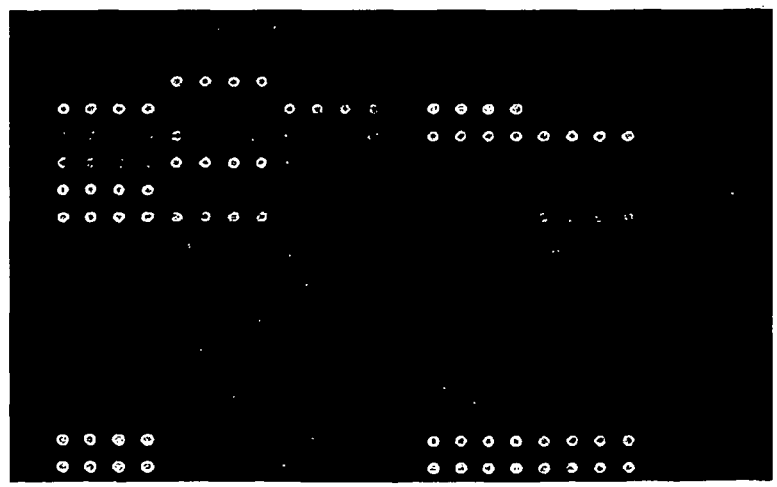
FIG. 12 is a photograph showing mouse spleen site specific immobilized hybridized oligonucleotides.

RNA extracted from whole mouse embryo at 9 days, as shown in FIG. 11, and from adult mouse spleen tissue, as shown in FIG. 12, using Promega's SV total RNA extraction system, was quality checked using an Agilent Bioanalyzer. The RNA was amplified by NuGen's Ovation method to yield about a 5000 times amplified aminoallyl-c-DNA. This was conjugated with Cy5-NHS ester to yield the fluorophor-labeled c-DNA. C-DNA yield was quantitated and the label incorporation ratio confirmed using a Nanodrop 1000 fiber-optic spectrophotometer. The Cy5-c-DNA (0.5 micrograms total c-DNA in 80 microliters) was hybridized on the site specific immobilized arrays 20 hours in 5×SSC+0.1% SDS. The arrays were washed successively in 3×SSC twice, 1×SSC twice and 0.1×SSC once, then spun dry. They site specific immobilized spot arrays were read using a PE ScanArray confocal scanning microscope at relatively low settings of laser <65% and gain <60%. Obtaining good results at these low settings indicates the c-DNA to be well labeled and that the epoxysilane substrate of the present invention retains optimal probe oligonucleotides for the target to hybridize.

Example 10

The Method of the Present Invention Applied to an Apt Device of the Present Invention; Microwell Devices to Optimize Analyte and Antibody Measurement by Least Energy Adsorption A proteomic microarray suitable for serodiagnosis of antipathogen antibody titer (APT Device) was prepared as follows. Serial dilutions of human IgG and IgM were printed as calibration standards, and bacterial and viral antigens were printed in triplicate as shown in the table below.

TABLE 10

Printed calibration standards and bacterial and viral antigens

| | | | |
|---|---|---|---|
| IgM 900 ug/ml | H. pylori | T. gondii | IgG 900 ug/ml |
| IgM 300 ug/ml | | | IgG 300 ug/ml |
| IgM 100 ug/ml | Herpes 1 | Rubella | IgG 100 ug/ml |
| IgM 33.3 ug/ml | | | IgG 33.3 ug/ml |
| IgM 11.1 ug/ml | Herpes 2 | Rubeola | IgG 11.1 ug/ml |
| IgM 3.7 ug/ml | | | IgG 3.7 ug/ml |
| IgM 1.2 ug/ml | CMV | C. trachomatis | IgG 1.2 ug/ml |
| IgM 0.4 ug/ml | | | IgG 0.4 ug/ml |
| IgM 0.14 ug/ml | EBV | C. jejuni | IgG 0.14 ug/ml |
| IgM 0 ug/ml | | | IgG 0 ug/ml |

The surface was blocked with 1% BSA in Tris-Buffered saline pH 8 (blocking buffer) for 18 hours. Serum samples from patients known to have been infected with *Helicobacter pylori* (*H. pylori*), and tested for their antibody titer by reference methods, were diluted 1 in 10 by volume in blocking buffer. These diluted samples were then incubated, 200 uL of each sample per well, on the microarrays for 15 minutes. The samples were decanted and the wells washed by two cycles of filling the wells with Phosphate-buffered saline pH 7.4, shaking for 20 seconds, and decanting. A third wash of 20 seconds was done with blocking buffer. The wells were then filled with 200 uL of a combination of goat-anti-humanIgG.Cy3 conjugate 3 ug/ml and goat-anti-human IgM.Dy647 conjugate in blocking buffer and incubated for 15 minutes. The conjugates were decanted and the wells washed by two cycles of filling the wells with Phosphate-buffered saline pH 7.4, shaking for 20 seconds, and decanting. The plastic sides of the wells were removed with a wedge leaving the flat slide glass bottom, which was washed for 20 seconds in deionized water and dried by spinning it in the centrifuge at 500 RPM for 1 minute.

Figure 13:
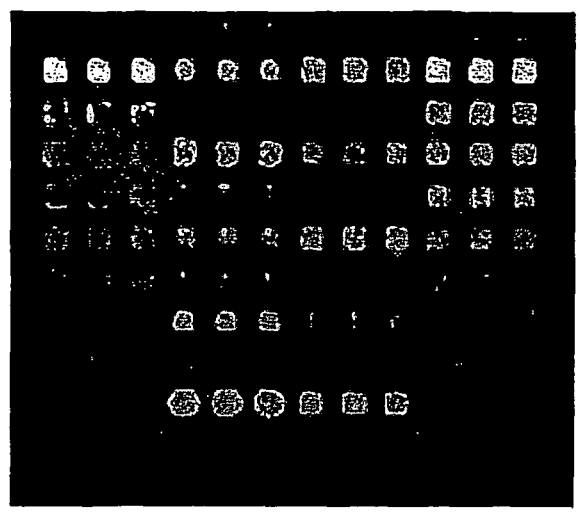
FIG. 13 is a photograph showing a patient. IgG and IgM serum responses to ten pathogen microarray plus IgG and IgM calibration standards.

A Perkin Elmer ScanArray laser scanning confocal microscope was used to image the arrays at the following settings: Cy3 (green) channel (IgG) laser 70% photomultiplier 70%, Cy5 (red) channel (IgM) laser 75% photomultiplier 75%. An array image representative of the experiment is shown in FIG. 13. A multiplex proteomic, diagnostic assay, conducted in approximately 35 minutes, is thus provided that gives quantitative titers of IgG and IgM in patient sera against ten human pathogens.

Those skilled in the art will recognize, or be able to ascertain using no more than routine experimentation, many equivalents to the embodiments of the invention described specifically above. Such equivalents are intended to be encompassed in the scope of the following claims.

What is claimed is:

1. A method of making an assay device for conducting an assay to detect a concentration of an analyte in a sample fluid, the method comprising:
    applying an epoxysilane coating to a surface of an assay device to provide the assay device with hydrophobic linking sites, hydrophilic linking sites, and covalent linking sites;
    modulating the ratio of hydrophobic linking sites to hydrophilic linking sites to covalent linking sites using baking time and temperature of the epoxysilane coating so as to optimize the binding of proteins and antibodies on the surface of the assay device;
    printing a calibration dot on the surface of the assay device under constant humidity control, the calibration dot including a predetermined quantity of analyte, wherein the analyte is a protein or an antibody, the calibration dot including a modulation buffer;
    printing a test dot on the surface of the assay device under constant humidity control, the test dot including a capture antibody for binding the analyte, the test dot further including the modulation buffer;
    wherein the test dot and the calibration dot have molecular layer thickness, and
    wherein the modulation buffer is $H_3BO_3$ at pH 5.0.

2. The method of claim 1, wherein printing the test dot and the calibration dot on the surface is carried out under conditions of constant relative humidity in the range of 15% to 90%.

3. The method of claim 1, wherein the surface is substantially planar.

4. The method of claim 3, wherein the surface includes a loading portion for receiving the sample fluid and a reading portion for receiving the sample fluid from the loading portion, the calibration dot and the test dot being printed on the reading portion.

5. The method of claim 1, wherein the modulation buffer contains a molecular spacer.

6. The method of claim 1, wherein the assay device includes a multiplex of immobilized gradient test spot arrays and calibration dot arrays.

7. The method of claim 5, wherein the site-specific immobilized calibration dot displays evenly dispersed analyte.

8. The method of claim 5, wherein the site-specific immobilized calibration dot displays evenly dispersed analyte with minimized steric hindrance.

* * * * *